United States Patent [19]
LeMaster et al.

[11] Patent Number: 4,774,036
[45] Date of Patent: Sep. 27, 1988

[54] METHOD OF MAKING AN INTRAOCULAR LENS

[75] Inventors: William LeMaster, Goleta, Calif.; Dennis T. Grendahl, Excelsior Bay Gables, Excelsior, Minn. 55331

[73] Assignee: Dennis T. Grendahl, Orono, Minn.

[21] Appl. No.: 41,235

[22] Filed: Apr. 22, 1987

Related U.S. Application Data

[62] Division of Ser. No. 761,408, Aug. 1, 1985, Pat. No. 4,676,791.

[51] Int. Cl.$^4$ .............................................. B29D 11/00
[52] U.S. Cl. ...................................... 264/1.7; 264/2.7; 264/78; 264/245; 264/291
[58] Field of Search ................... 264/1.7, 2.7, 1.1, 2.6, 264/78, 245, 291; 51/284 R, 284 E; 623/6

[56] References Cited

U.S. PATENT DOCUMENTS

| | | | |
|---|---|---|---|
| 3,454,332 | 7/1969 | Siegel | 264/1.7 |
| 3,718,383 | 2/1973 | Moore | 264/1.7 |
| 4,460,523 | 7/1984 | Neefe | 264/1.7 |
| 4,558,931 | 12/1985 | Fuhrman | 264/1.7 |
| 4,605,409 | 8/1986 | Kelman | 623/6 |
| 4,619,662 | 10/1986 | Juergens, Jr. | 623/6 |
| 4,629,460 | 12/1986 | Dyer | 623/6 |

FOREIGN PATENT DOCUMENTS 2124500 2/1984 United Kingdom ................ 264/1.7

OTHER PUBLICATIONS

Rayner and Keeler Limited, Catalogue No. 469, 2 pages.

*Primary Examiner*—James Lowe
*Attorney, Agent, or Firm*—Hugh D. Jaeger

[57] ABSTRACT

A color ringed or rimmed edge intraocular lens for implant in either the anterior chamber, the posterior chamber or the cornea of the eye. The lens has a colorless or clear central region of a material such as polymethylmethacrylate (PMMA) and a peripheral surrounding portion of a dark material such as blue PMMA. Polysulfone can also be utilized. The lens can be fabricated by passing a clear rod of optical quality PMMA through an extrusion orifice and coating the circumference of the rod with a layer of predetermined thickness of colored, preferably blue PMMA or other compatible material. Other methods of fabrication can include the introduction of a suitable dye into the outer regions of the rod, or joining the clear central region to a ring of colored material by thermal adhesive bonding or other known processes.

4 Claims, 5 Drawing Sheets

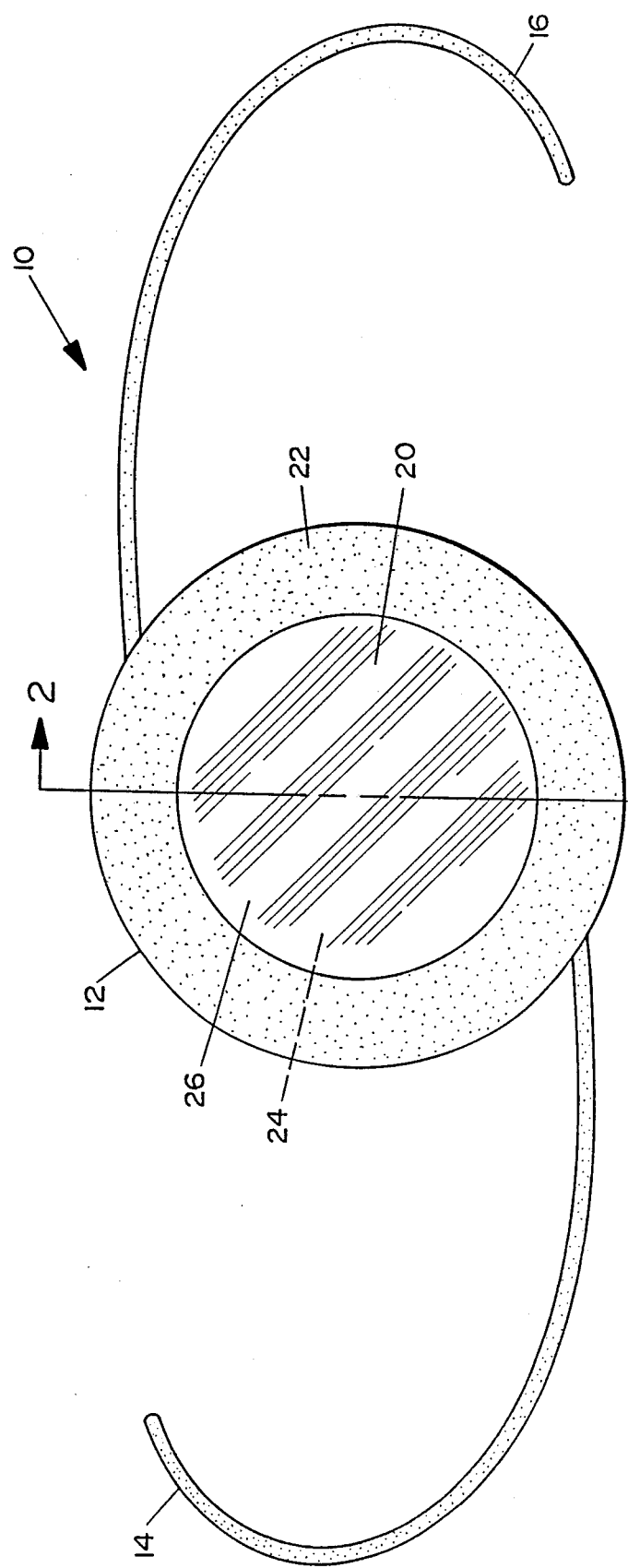
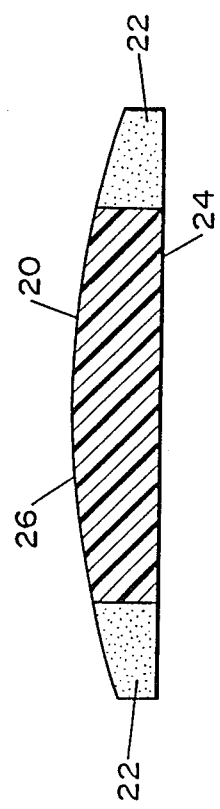
FIG. 1
FIG. 2

METHOD OF MAKING AN INTRAOCULAR LENS

This application is a divisional of application Ser. No. 761,408, filed Aug. 1, 1985, and now U.S. Pat. No. 4,676,791.

BACKGROUND OF THE INVENTION

1. Field of the Invention

The present invention relates to intraocular lenses including a ring or rim of colored material, and more particularly, pertains to the reduction of glare resulting from the edge effect and from the light transmitted from the positioning loops to the lens itself.

2. Description of the Prior Art

None of the prior art lenses known to applicant have utilized structure for reduction of glare resulting from the edge effect and from the light transmitted through the positioning loops to the lens itself.

The edges of a lens are known to cause glare as a result of the light which is incident on the lens but which is not brought to a focus on the retina. Because the loops are generally made from the same material as the central portion, the light falling on the loops is transmitted to the lens itself, causing glare and reflections which are distracting and uncomfortable.

The present invention overcomes the disadvantages by providing a darker region which reduces the intensity of the light transmitted from the edge of the lens and from positioning loops to the central region.

SUMMARY OF THE INVENTION

The general purpose of the present invention is to provide an intraocular lens or intracorneal lens with a ring or rim of colored material which minimizes glare, and distracting reflections caused by the edge effect and from the light transmitted from the positioning loops to the lens itself.

One preferred embodiment of the present invention is a lens which has a ring or rim peripheral portion which is a darker color, serving to reduce the intensity of the light transmitted through the loops to the central portion of the lens. The lens can be an anterior chamber lens or posterior chamber lens with loop or an intracorneal lens.

One preferred method of fabrication is to coat a clear rod or boule of PMMA with a darker outer layer through an extrusion process. Alternative methods of manufacture include the introduction of a dye into the outer layers of the clear rod PMMA rod.

Having thus described several embodiments of the present invention, it is the principal object hereof to provide an intraocular or intracorneal lens which is substantially devoid of glare and reflections caused by light transmitted to the lens through the positioning loops, holes, or edges of the lens.

One object of the present invention is to provide a method for fabrication of an intraocular lens which possesses improved quality of vision because of the reduced glare and reflections normally introduced by the positioning loops or edges of the lens.

Another object of the present invention is to provide cylindrical boule member with a colored ring or rim, which lens can be lathe cut.

A further object of the present invention are positioning holes and radial loop holes in the colored ring minimizing glare from the holes.

An additional object of the present invention is a single-piece positive lens with colored haptics.

BRIEF DESCRIPTION OF THE DRAWINGS

FIG. 1 illustrates a top view of an intraocular lens showing the dark peripheral portion according to the present invention;

FIG. 2 illustrates a sectional view along the line 2—2 of the lens shown in FIG. 1;

DETAILED DESCRIPTION OF THE PREFERRED EMBODIMENTS

Figure 3:
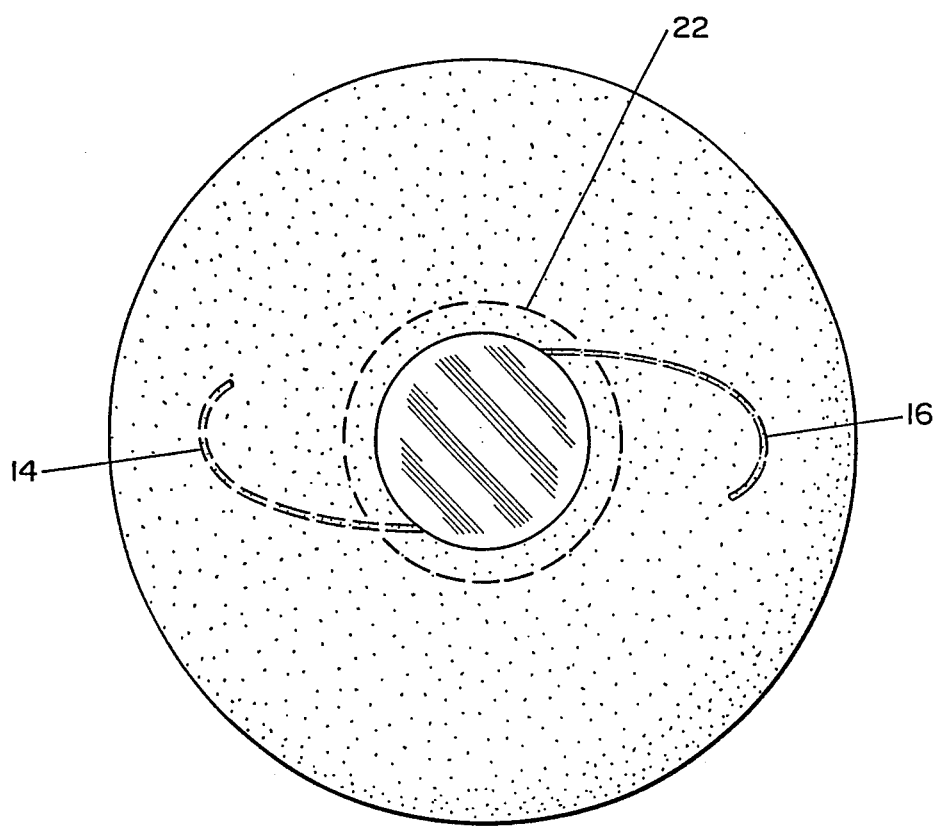
FIG. 3 is across sectional view of a rod of transparent material ringed dark material.

FIG. 1 illustrates an intraocular lens 10 including a lens optic 12 and two positioning loops 14 and 16. The lens optic 12 includes a clear central portion 20 and a colored peripheral portion 22. The entire assembly is made of any suitable material, preferably PMMA or alternative materials such as polysulfone.

The colored ring or rim portion 22 is sufficiently darker in color to substantially reduce the intensity of light transmitted from the outer edge to the clear central portion 20. While the transmissivity of the portion 22 is preferably reduced by coloring with a darker color than the transparent section, such as blue, the transmissivity can be reduced by other processes as well. The width of the colored portion 22 is selected to provide adequate space for the attachment of the loops 14 and 16 by processes such as staking, adhesive bonding, or ultrasonic bonding. The width of the colored portion 22 is also sufficient to provide adequate reduction in the intensity of the light transmitted from the periphery 12 to the central portion 20 of the lens 10. The loops 14 and 16 shown are made of colored material. This further reduces the intensity of the light transmitted to the clear central portion 20. Alternatively, the loops can be made of clear material similar to that used in the central portion 20. The same discussion applies to intracorneal lens and the edge effect of course. The diameter of the clear and colored portions are predetermined based on the specific design of the lens. Positioning holes or locating holes 18a–18n are provided in the colored area, as are radial loop holes 15 and 17 for securing loops to the lens optic 12.

FIG. 2 shows a sectional view of the lens of FIG. 1 along the line 2—2. The colored portion 12 extends annularly from the rear surface 24 to the front surface 26.

FIG. 3 shows as cross section of a rod. The lens and loops can be lathed from a single rod of material as illustrated FIG. 3 where the darker outer ring is blue and the center portion clear. The lens loops as such could be lathe cut as illustrated in dashed lines.

Figure 4A:
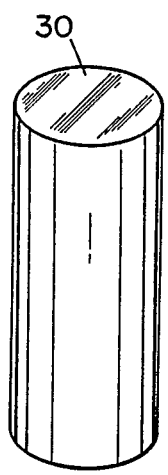
FIGS. 4a, 4b, and 4c show the material used to fabricate the lens in various stages of manufacture.
Figure 4B:
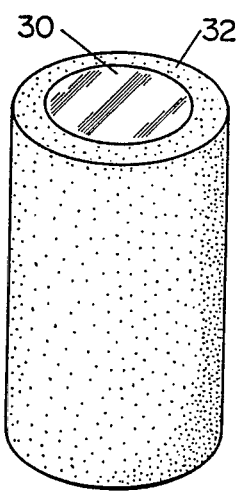
Figure 4C:
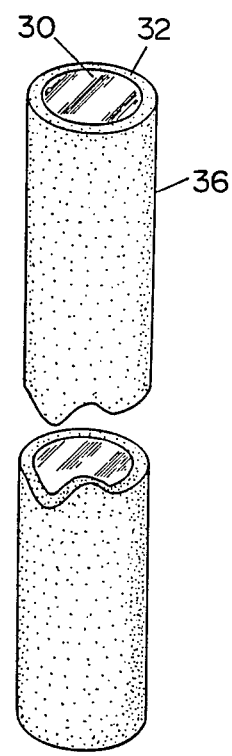

FIGS. 4a, 4b, and 4c illustrate various stages in the fabrication of the rod from which lenses are cut by conventional means. The initial rod or boule 30 of clear PMMA is substantially larger in diameter than the finished lens, and can be as long as is convenient to handle. The boule 30 is then coated with a uniform layer 32 of colored PMMA as shown in FIG. 4b.

The colored layer 32 can be applied to the boule 30 by passing the boule 30 through an extrusion die having a diameter selected to apply the colored layer 32 over the desired thickness of layer 30. Alternatively, the colored layer 32 could be fabricated as a tube and the clear inner portion 30 applied by extruding it into the central portion of the tube or by other known processes. The resulting article is then heated and drawn to the desired diameter in the range of 6 mm to 9 mm as shown in FIG. 4c. The drawn rod 36 provides the raw stock from which the lenses can be lathe cut by conventional processes.

Figure 5A:
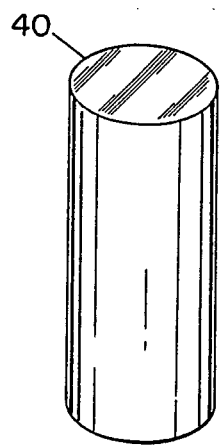
FIGS. 5a, 5b, and 5c show the material used to fabricate the lens at various stages of an alternate method of manufacture; and, FIG. 6 illustrates an enlarged view of the portion of FIG. 5b enclosed in dotted line.
Figure 5B:
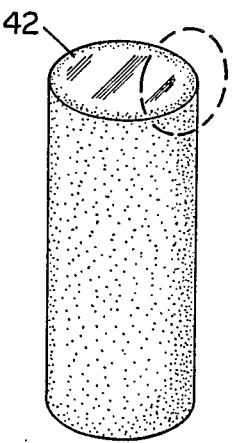
Figure 5C:
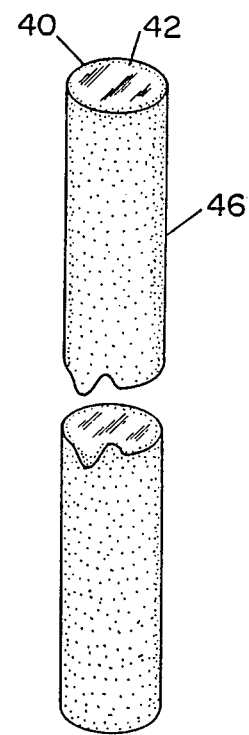

FIGS. 5a, 5b, and 5c illustrate an alternative method of manufacture. The clear PMMA rod or boule 40 has a diameter substantially greater than the diameter of the finished lens. The boule 40 is then treated with a suitable dye, preferably blue in color, to create a colored outer layer 42, as shown in FIG. 5b, which is effective to reduce the transmission of light from the periphery of the finished lens to the central portion. The resulting article 46 is then heated and drawn to the desired finished diameter as illustrated in FIG. 5c.

Figure 6:
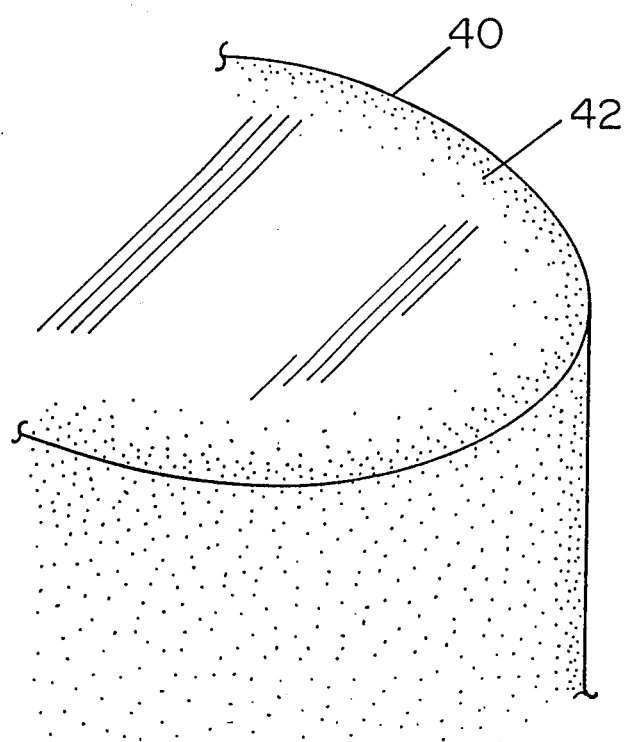

FIG. 6 is an enlarged view of the portion of FIG. 5b enclosed with the dotted line. It can be observed that the colored portion 42 is actually a graded region, being darker at the periphery and lighter toward the center of the boule. The range of the gradation can be controlled by the degree of reduction in diameter as the boule is drawn. The greater the degree of reduction in diameter, the sharper the optical gradient as a function of $1/R^2$. This technique can be used to provide the most suitable gradient.

While it is contemplated that the intermediate product of FIGS. 4b and 5b will be the preferred technique for fabrication of the lenses, it is also possible to draw a clear boule to the desired finished diameter and then introduce the dye to form the layer 42.

The preferred embodiments are shown with discrete positioning loops which are attached to the lens. Alternatively, and most preferably, the lens and loops can be fabricated such as by lathe cutting from a single piece of PMMA or polysulfone having a clear central portion and a colored peripheral portion. Likewise, an intracorneal lens is made by lathe cutting.

Full advantages of the invention are obtained when the lens has a clear central portion, and a colored ring or rimmed peripheral portion and colored loops. In some situations it can be desirable to color only the edge of the lens. By lathing loops from the colored portion of the rod and lathing the optic from the clear portion of the rod, there is manufactured a single piece lens with colored loops and partially colored optic.

It is claimed:

1. A process for making an intraocular lens having a clear central lens portion and a peripheral lens portion, said peripheral lens portion having a reduced, graded transmissivity ranging from lowest at the outer extremity thereof to highest at the junction with said clear central lens portion, and peripheral lens portion extending completely about the periphery of said clear central lens portion, the process comprising:
   a. forming a cylinder of appropriate material, larger in diameter than the diameter of the lens to be made;
   b. forming a colored layer on the surface of the cylinder produced in step (a);
   c. heating and drawing the cylinder produced in step (b) to an appropriate diameter whereby graded transmissivity is obtained, the degree depending on the amount of drawing; and,
   d. lath cutting the cylinder produced in step (c) to form the lens.

2. The process of claim 1 in which step (b) is performed by extruding a layer of colored material on the surface of the cylinder produced in step (a).

3. The process of claim 1 in which step (b) is performed by dyeing the surface of the cylinder produced in step (a).

4. A process as in any preceding claim in which the lens to be made bears positioning loops attached to the peripheral portion of the lens, and the loops are fabricated, together with the lens, in step (d).

* * * * *